United States Patent

Regnier et al.

[11] 4,177,272
[45] Dec. 4, 1979

[54] DISUBSTITUTED PIPERAZINES

[75] Inventors: Gilbert Regnier, Chatenay-Malabry; Roger Canevari, Elancourt; Michel Laubie, Vaucresson; Jean-Claude Poignant, Bures sur Yvette, all of France

[73] Assignee: Science Union et Cie, Suresnes, France

[21] Appl. No.: 864,204

[22] Filed: Dec. 27, 1977

[30] Foreign Application Priority Data

Dec. 31, 1976 [GB] United Kingdom ............... 54398/76

[51] Int. Cl.² .................... A61K 31/50; C07D 417/14
[52] U.S. Cl. .................................. 424/250; 544/366; 544/367
[58] Field of Search ................. 260/268 BC; 424/250; 544/367

[56] References Cited

U.S. PATENT DOCUMENTS

| | | | |
|---|---|---|---|
| 3,489,757 | 1/1970 | Koppe et al. | 260/268 BC |
| 3,808,210 | 4/1974 | Regnier et al. | 260/268 BC |
| 3,917,597 | 11/1975 | Regnier et al. | 424/250 |
| 3,944,551 | 3/1976 | Regnier et al. | 260/268 BC |

Primary Examiner—Paul M. Coughlan, Jr.
Attorney, Agent, or Firm—Omri M. Behr

[57] ABSTRACT

Disubstituted piperazines of the formula:

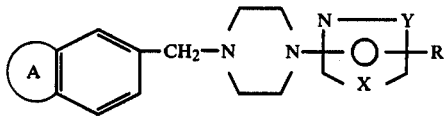

wherein:

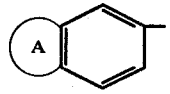

is naphthyl, benzo [b] furanyl, benzo [b] thienyl, benzodioxolyl, benzodioxanyl, benzodioxacycloheptanyl, coumaranyl, chromanyl, $\Delta^3$-chromenyl, thiochromanyl or $\Delta^3$-thiochromenyl, X is nitrogen and simultaneously Y is oxygen or sulfur, or X is sulfur, imino (NH) or methylimino (N $CH_3$) and simultaneously Y is nitrogen, and R is hydrogen, lower alkyl, phenyl, halophenyl, loweralkylphenyl or lower alkoxyphenyl.

These compounds possess interesting pharmacological and therapeutic properties, and may be used as medicines, especially in the treatment of hypertension, peripheral vascular disorders and Parkinson's disease.

7 Claims, No Drawings

DISUBSTITUTED PIPERAZINES

The present invention provides disubstituted piperazines of the formula I:

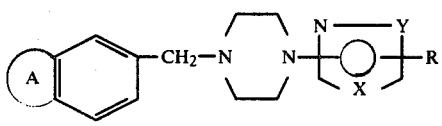

and acid addition salts, especially physiologically tolerable acid addition salts thereof,
wherein:
A is selected from the group consisting of a benzene ring, and 5-, 6- and 7-membered heterocyclic rings having one and two double bonds and one and two hetero atoms selected from oxygen and sulfur atoms, so that the group

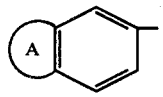

is selected from the group consisting of naphthyl, benzo [b] furanyl, benzo [b] thienyl, benzodioxolyl, benzodioxanyl, benzodioxacycloheptanyl, coumaranyl, chromanyl, $\Delta^3$-chromenyl, thiochromanyl and $\Delta^3$-thiochromenyl radicals,
X is a nitrogen atom and simultaneously Y is selected from the group consisting of an oxygen atom and a sulfur atom, or
X is selected from the group consisting of a sulfur atom, an amino radical (NH) and a methylimino radical (NCH$_3$), and simultaneously Y is a nitrogen atom, and R is selected from the group consisting of a hydrogen atom, an alkyl radical having from 1 to 5 carbon atoms inclusive, a phenyl radical, halophenyl radicals, alkylphenyl and alkoxyphenyl radicals wherein the alkyl moieties have from 1 to 5 carbon atoms inclusive.

In the meaning of R, the halogen atoms may be, for example, chlorine, fluorine or bromine atoms, the alkyl moieties may be methyl, ethyl, propyl, butyl or pentyl radicals and the alkoxy moieties may be methoxy, ethoxy, propoxy, butoxy and pentyloxy radicals.

Due to their pharmacological properties, the preferred compounds are the compounds of the formula I wherein A is as defined above, X is a sulfur atom, Y is a nitrogen atom and R is a hydrogen atom, and physiologically tolerable acid addition salts thereof.

Among these preferred compounds, the most interesting compounds are those having the formula I wherein X, Y and R are as defined in the above paragraph and

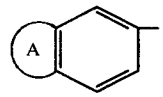

is selected from the group consisting of benzo [b] furanyl, benzodioxolyl, benzodioxanyl and coumaranyl radicals, and physiologically tolerable acid addition salts thereof.

The compounds of the general formula I are new and they were prepared according to the following methods which are all included in the present invention.

The present invention provides a process for preparing a compound of the general formula I which comprises:
condensing a halo compound of the general formula II:

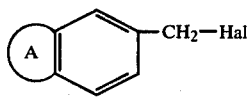

in which A has the meaning given above and Hal is a chlorine or a bromine atom, with a N-monosubstituted piperazine of the general formula III:

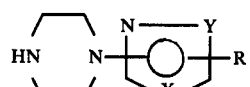

in which X, Y and R have the meanings given above; or condensing a halo compound of the general formula IV:

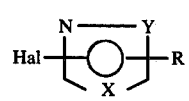

in which X, Y, R and Hal have the meanings given above, with a N-monosubstituted piperazine of the general formula V:

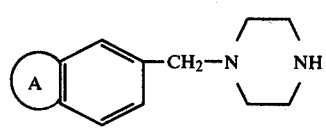

in which A has the meaning given above.

The above processes are advantageously carried out in solution in a polar solvent, for example an alcohol having a high boiling point, for example butanol or pentanol, or preferably an aliphatic amide, for example dimethyl formamide. The processes are advantageously carried out at a temperature of from 110° to 140° C. in the presence of an acceptor for the hydrogen halide formed in the course of the reaction. As acceptors, there may be mentioned, for example, alkali metal and alkaline-earth metal salts of carbonic acid, for example sodium and potassium bicarbonates and carbonates and calcium carbonate, and organic bases for example dimethylamine, pyridine and triethylamine; if desired, there may be used an excess of the monosubstituted piperazine of the formula III or V, the excess acting as the acid acceptor.

The present invention also provides a process for preparing a compound of the general formula I which comprises submitting a mixture of an aldehyde of the general formula VI:

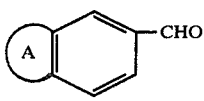

in which A has the meaning given above, and a N-monosubstituted piperazine of the general formula III given above, to an alkylating reduction using hydrogen at a pressure of from 5 to 7 atmospheres, in the presence of a small quantity of palladium-on-charcoal in a slightly polar aprotic solvent, for example, ethyl acetate.

Such a process is advantageously carried out by submitting to hydrogenation under a hydrogen pressure of from 5 to 7 atmospheres, a substantially equimolecular mixture of the compounds of the formulae III and VI, in solution in ethyl acetate, in the presence of a quantity of palladium-on-charcoal such that the weight of palladium is from 0.15 to 0.2% of the total weight of the reactants of the formulae III and VI at a temperature of from 50° to 80° C.

The starting materials used for these processes are known compounds, or they may be prepared according to methods described in the literature for preparing similar compounds, as mentioned in the following examples.

The compounds of the general formula I are weak bases which may be converted by treatment with acids into acid addition salts. As acids which may be used for the formation of these addition salts, there may be mentioned for example, in the mineral series: hydrochloric, hydrobromic, sulfuric, and phosphoric acids, and in the organic series: acetic, propionic, maleic, fumaric, tartaric, citric, oxalic, benzoic, methanesulphonic and isethionic acids.

The compounds of the formula I may be purified by physical methods, for example by distillation, crystallization or chromatography, or by chemical methods, for example by formation of an addition salt followed by crystallization of the latter and decomposition thereof with an alkaline agent.

The compounds of the general formula I possess valuable pharmacological and therapeutic properties, especially anti-hypertensive, peripheral vasodilating, dopaminergic agonistic and anti-Parkinson properties. They may therefore, be used as medicines, especially in the treatment of hypertension, peripheral vascular disorders and Parkinson's disease.

Their toxicity is low and their $LD_{50}$ determined in mice by intraperitoneal route is higher than 200 mg/kg.

Their neurologic properties were evidenced in the rats and mice by modifications observed on the stereotypy, motility and excitation.

In mice, the average effective dose is about 50 mg/kg by intraperitoneal route. At this dose, there were observed a decrease of motility and tonus.

The scores of CNS stimulation or stereotypy were determined according to the method of Quinton and Halliwell, Nature 200 No. 4902, p. 178 (1963). The scores for 3 hours raised up to 246 with a dose of 40 mg/kg I.P. and up to 261 with a dose of 80 mg/kg I.P.

Furthermore, when administered to the dog intravenously at doses of 0.5 to 2 mg/kg, an increase of the femoral output of up to 40% is observed durably.

The present invention therefore provides a pharmaceutical composition comprising as active ingredient a compound of the general formula I or a physiologically tolerable acid addition salt thereof in admixture or conjunction with a pharmaceutically suitable carrier, such for example, as distilled water, glucose, lactose, starch, talc, magnesium stearate, ethyl cellulose or cocoa butter.

The so-obtained pharmaceutical compositions are advantageously in unit dosage form and may contain from 30 to 100 mg of the active ingredient.

These pharmaceutical compositions may be in form of tablets, dragees, capsules, suppositories, injectable or drinkable solution and may be administered by oral, rectal or parenteral route at a dose of 30 to 100 mg, 1 to 5 times a day.

The following examples illustrate the invention, the melting points being determined in a capillary tube.

EXAMPLE 1

1-piperonyl-4-(1,3,4-thiadiazol-2-yl) piperazine

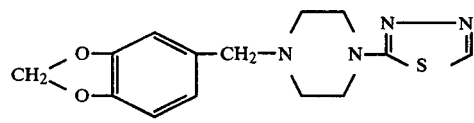

First method

To a solution of 5.1 g (0.03 mole) of piperonyl chloride (cf. French Patent No. 1,312,427) in 60 ml of dimethylformamide, there were added 7.3 g (0.03 mole) of 1-(1,3,4-thiadiazol-2-yl)-piperazine dihydrochloride (melting at 220° C. with decomposition) and 6.4 g (0.06 mole) of dried sodium carbonate.

The reaction mixture was heated at 120° C. for 10 hours. Then, the sodium chloride formed was filtered off and the dimethylformamide was evaporated off under reduced pressure. The residue was taken up in 100 ml of benzene and 100 ml of water; the organic layer was decanted off and the solvent was evaporated off under reduced pressure. There were obtained 10 g of crystals which were recrystallized from 20 ml of ethanol. There were finally obtained 5.6 g of 1-piperonyl-4-(1,3,4-thiadiazol-2-yl)-piperazine melting at 111°–112° C.

The starting 1-(1,3,4-thiadiazol-2-yl)-piperazine was prepared by hydrolyzing with alcoholic potassium hydroxide the crude formyl derivative, itself prepared by condensing 1-formyl piperazine with 2-bromo-1,3,4-thiadiazole melting at 74° C. (Goerdeler and al., Ber 89 1534 (1956)).

Second method

A solution of 11.2 g (0.0678 mole) of 2-bromo-1,3,4-thiadiazole and 29.8 g (0.136 mole) of 1-piperonyl piperazine (cf. French Patent No. 1,312,427) in 400 ml of anhydrous dimethylformamide was heated at 110° C. for 8 hours. Then, the solvent was evaporated off under reduced pressure and the oily residue was taken up in 200 ml of benzene and 400 ml of water. The organic layer was decanted off then concentrated under reduced pressure. There was obtained a crystalline residue which recrystallized from 60 ml of ethanol, gave 9.9 g of crystals of 1-piperonyl-4-(1,3,4-thiadiazol-2-yl)-piperazine, melting at 112°–114° C.

Third method

A solution of 15 g (0.1 mole) of 3,4-methylenedioxybenzaldehyde and 24.3 g (0.1 mole) of 1-(1,3,4-thiadiazol-2-yl)-piperazine in 150 ml of ethyl acetate was hydrogenated under a hydrogen pressure of from 5 to 7 atmospheres, in the presence of from 2 to 5 g of palladised charcoal containing 10% of palladium, at a temperature of 50° C.

After absorption of the theoretical amount of hydrogen, the catalyst was filtered off and the solvent was evaporated off under reduced pressure.

There were obtained 27 g of a crystalline residue which, recrystallized from 150 ml of ethanol, gave 17 g of 1-piperonyl-4-(1,3,4-thiadiazol-2-yl) piperazine, melting at 112° C.

EXAMPLES 2 to 19

The following compounds were prepared according to the processes described in Example 1:

2. 1-(2-naphthylmethyl)-4-(1,3,4-thiadiazol-2-yl)-piperazine, M.P. 110°–112° C. (ethanol) starting from:
   2-bromomethylnaphthalene and 1-(1,3,4-thiadiazol-2-yl)-piperazine, or
   1-(2-naphthylmethyl)-piperazine and 2-bromo-1,3,4-thiadiazole, or
   β-naphthaldehyde and 1-(1,3,4-thiadiazol-2-yl)-piperazine.
3. 1-(3,4-ethylenedioxybenzyl)-4-(1,3,4-thiadiazol-2-yl)-piperazine, M.P. 116°–117° C. (ethanol) starting from:
   3,4-ethylenedioxybenzyl chloride (cf. French Patent No. 1,311,316) and 1-(1,3,4-thiadiazol-2-yl)-piperazine, or
   1-(3,4-ethylenedioxybenzyl)-piperazine (cf. French Patent No. 1,311,316) and 2-bromo-1,3,4-thiadiazole, or
   3,4-ethylenedioxybenzaldehyde (cf. Tomita, Chem. Abstracts 51 14728 (1957) and 1-(1,3,4-thiadiazol-2-yl)-piperazine.
4. 1-(5-coumaranylmethyl)-4-(1,3,4-thiadiazol-2-yl)-piperazine, M.P. 103°–104° C. (ethanol) starting from:
   5-coumaranylmethyl chloride (cf. Baddeley and al. Soc. (1956) 2458) and 1-(1,3,4-thiadiazol-2-yl) piperazine, or
   1-(5-coumaranylmethyl)-piperazine (prepared according to the method of Steward and al. J. Org. Chem. 13, 134 (1948)) and 2-bromo-1,3,4-thiadiazole, or
   5-coumaranaldehyde (preparing according to Baddeley and al. Soc. (1956) 2458) and 1-(1,3,4-thiadiazol-2-yl)-piperazine.
5. 1-(5-coumaranylmethyl)-4-(5-methyl-1,3,4-thiadiazol-2-yl)-piperazine, M.P. 116°–118° C. (ethanol), starting from:
   5-coumaranylmethyl chloride and 1-(5-methyl-1,3,4-thiadiazol-2-yl)-piperazine, or
   1-(5-coumaranylmethyl)-piperazine and 5-methyl-2-bromo-1,3,4-thiadiazole, or
   5-coumaranaldehyde and 1-(5-methyl-1,3,4-thiadiazol-2-yl)-piperazine.
6. 1-(5-benzo [b] thienylmethyl)-4-(5-methyl-1,3,4-thiadiazol-2-yl)-piperazine, M.P. 134°–136° C. (ethanol) starting from:
   5-benzo [b] thienylmethyl bromide (cf. Y. Matsuki and al. Chem. Abstracts 65 15301 (1966)) and 1-(5-methyl-1,3,4-thiadiazol-2-yl)-piperazine, or
   1-(5-benzo [b] thienylmethyl)-piperazine (prepared according to the method of Steward and al. J. Org. Chem. 13 134 (1948)) and 5-methyl-2-bromo-1,3,4-thiadiazole, or
   5-benzo [b] thienyl aldehyde (cf. Swiss Patent No. 442,353) and 1-(5-methyl-1,3,4-thiadiazol-2-yl)-piperazine.
7. 1-piperonyl-4-(5-methyl-1,3,4-thiadiazol-2-yl)-piperazine, M.P. 88°–90° C. (purified by liquid chromatography) starting from:
   piperonyl chloride and 1-(5-methyl-1,3,4-thiadiazol-2-yl)-piperazine, or
   1-piperonyl-piperazine and 5-methyl-2-bromo-1,3,4-thiadiazole, or
   3,4-methylenedioxybenzaldehyde and 1-(5-methyl-1,3,4-thiadiazol-2-yl)-piperazine.
8. 1-(3,4-ethylenedioxybenzyl)-4-(5-methyl-1,3,4-thiadiazol-2-yl)-piperazine, M.P. 110°–111° C. (purified by liquid chromatography) starting from:
   3,4-ethylenedioxybenzyl chloride and 1-(5-methyl-1,3,4-thiadiazol-2-yl)-piperazine, or
   1-(3,4-ethylenedioxybenzyl)-piperazine, and 5-methyl-2-bromo-1,3,4-thiadiazole, or
   3,4-ethylenedioxybenzaldehyde and 1-(5-methyl-1,3,4-thiadiazol-2-yl)-piperazine.
9. 1-(3,4-trimethylenedioxybenzyl)-4-(1,3,4-thiadiazol-2-yl)-piperazine, M.P. 104°–107° C. (acetonitrile/petroleum ether), starting from:
   3,4-trimethylenedioxybenzyl chloride and 1-(1,3,4-thiadiazol-2-yl)-piperazine, or
   1-(3,4-trimethylenedioxybenzyl)-piperazine and 2-bromo-1,3,4-thiadiazole, or
   3,4-trimethylenedioxybenzaldehyde and 1-(1,3,4-thiadiazol-2-yl)-piperazine.
10. 1-(5-benzo [b] furanylmethyl)-4-(1,3,4-thiadiazol-2-yl)-piperazine, M.P. 98°–99° C. (purified by liquid chromatography), starting from:
    5-benzo [b] furanylmethyl chloride (cf. A. Areschka and al. Chim. Therap. 7, 337 (1972)) and 1-(1,3,4-thiadiazol-2-yl)-piperazine, or
    1-(5-benzo [b] furanylmethyl)-piperazine (prepared according to the method of Steward and al. J. Org. Chem. 13 134 (1948)) and 2-bromo-1,3,4-thiadiazole, or
    5-benzo [b] furanyl aldehyde (cf. Glodenberg and al. Chim. Therap. 1, 221 (1966)) and 1-(1,3,4-thiadiazol-2-yl)-piperazine.
11. 1-piperonyl-4-(1,2,4-triazol-3-yl)-piperazine, starting from:
    piperonyl chloride and 1-(1,2,4-triazol-3-yl)-piperazine, or 1-piperonyl-piperazine and 3-bromo-1,2,4-triazole (cf. Manchot and Noll, Lieb. Ann. 343 9 (1905)), or 3,4-methylenedioxybenzaldehyde and 1-(1,2,4-triazol-3-yl)-piperazine.
12. 1-(3,4-ethylenedioxybenzyl)-4-(1,2,4-triazol-3-yl)-piperazine, starting from:
    3,4-ethylenedioxybenzyl chloride and 1-(1,2,4-triazol-3-yl)-piperazine, or
    1-(3,4-ethylenedioxybenzyl)-piperazine and 3-bromo-1,2,4-triazole, or
    3,4-ethylenedioxybenzaldehyde and 1-(1,2,4-triazol-3-yl)-piperazine.
13. 1-piperonyl-4-(3-methyl-1,2,4-oxadiazol-5-yl)-piperazine, M.P. 225°–227° C. (methanol), starting from: piperonyl chloride and 1-(3-methyl-1,2,4-oxadiazol-5-yl)-piperazine, or
    1-piperonyl-piperazine and 3-methyl-5-chloro-1,2,4-oxadizole (cf. C. Mousseboy and Eloy, Helv. 47 838 (1964)), or 3,4-methylenedioxybenzaldehyde and 1-(3-methyl-1,2,4-oxadiazol-5-yl)-piperazine.
14. 1-(3,4-ethylenedioxybenzyl)-4-(3-methyl-1,2,4-oxadiazol-5-yl)-piperazine, M.P. 101°–102° C., starting from:
  3,4-ethylenedioxybenzyl chloride and 1-(3-methyl-1,2,4-oxadiazol-5-yl)-piperazine, or
  1-(3,4-ethylenedioxybenzyl)-piperazine and 3-methyl-5-chloro-1,2,4-oxadiazole, or 3,4-ethylenedioxybenzaldehyde and 1-(3-methyl-1,2,4-oxadiazol-5-yl)-piperazine.
15. 1-piperonyl-4-(1,2,4-thiadiazol-5-yl)-piperazine, M.P. 74° C. (ethanol), starting from:
  piperonyl chloride and 1-(1,2,4-thiadiazol-5-yl)-piperazine, or
  1-piperonyl piperazine and 5-bromo-1,2,4-thiadiazole (cf. J. Goerdeler and al. Ber. 90 182 (1957)), or
  3,4-methylenedioxybenzaldehyde and 1-(1,2,4-thiadiazol-5-yl)-piperazine.
16. 1-piperonyl-4-(3-methyl-1,2,4-thiadiazol-5-yl)-piperazine, M.P. 110°–111° C. (acetonitrile), starting from:
  piperonyl chloride and 1-(3-methyl-1,2,4-thiadiazol-5-yl)-piperazine, or
  1-piperonyl piperazine and 5-chloro-3-methyl-1,2,4-thiadiazole, or
  3,4-methylenedioxybenzaldehyde and 1-(3-methyl-1,2,4-thiadiazol-5-yl)-piperazine.
17. 1-(3,4-ethylenedioxybenzyl)-4-(3-methyl-1,2,4-thiadiazol-5-yl)-piperazine, M.P. 75°–76° C. (acetonitrile), starting from:
  3,4-ethylenedioxybenzyl chloride and 1-(3-methyl-1,2,4-thiadiazol-5-yl)-piperazine, or
  1-(3,4-ethylenedioxybenzyl)-piperazine and 5-chloro-3-methyl-1,2,4-thiadiazole, or
  3,4-ethylenedioxybenzaldehyde and 1-(3-methyl-1,2,4-thiadiazol-5-yl)-piperazine.
18. 1-(3,4-ethylenedioxybenzyl)-4-(1,2,4-thiadiazol-5-yl)-piperazine, M.P. 146°–148° C. (ethanol), starting from:
  3,4-ethylenedioxybenzyl chloride and 1-(1,2,4-thiadiazol-5-yl)-piperazine, or
  1-(3,4-ethylenedioxybenzyl)-piperazine and 5-bromo-1,2,4-thiadiazole, or
  3,4-ethylenedioxybenzaldehyde and 1-(1,2,4-thiadiazol-5-yl)-piperazine.
19. 1-piperonyl-4-(4-methyl-1,2,4-triazol-3-yl)-piperazine, M.P. 146°–148° C. (acetonitrile), starting from:
  piperonyl chloride and 1-(4-methyl-1,2,4-triazol-3-yl)-piperazine, or
  1-piperonyl piperazine and 4-methyl-3-bromo-1,2,4-triazole (cf. G. Barlin, Soc. (B) 1967 p. 641), or
  3,4-methylenedioxybenzaldehyde and 1-(4-methyl-1,2,4-triazol-3-yl)-piperazine.

The following examples illustrate the pharmaceutical compositions containing as active ingredient, a compound of the general formula I.

EXAMPLE 20

Formulation for one injectable ampule containing 5 mg of active ingredient

| | |
|---|---|
| 1-(3,4-ethylenedioxybenzyl)-4-(1,3,4-thiadiazol-2-yl)-piperazine methane sulfonate | 0.0065 g |
| Mannitol | 0.050 g |
| Distilled water for injectable preparation q.s.p. | 2 ml |

EXAMPLE 21

Formulation for one injectable ampule containing 5 mg of active ingredient

| | |
|---|---|
| 1-(5-benzo [b] furanylmethyl)-4-(1,3,4-thiadiazol-2-yl)-piperazine bis methane sulfonate | 0.0082 g |
| Mannitol | 0.050 g |
| Distilled water for injectable preparation q.s.p. | 2 ml |

EXAMPLE 22

Formulation for one capsule containing 50 mg of active ingredient

| | |
|---|---|
| 1-piperonyl-4-(1,3,4-thiadiazol-2-yl)-piperazine methanesulfonate | 0.066 g |
| Microcristalline cellulose | 0.082 g |
| Carboxymethyl starch | 0.006 g |
| Colloidal silica | 0.0005 g |
| Talc | 0.0055 g |

We claim:
1. A compound of the formula

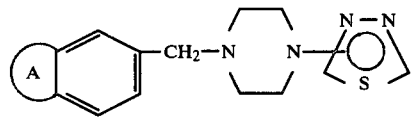

wherein the group

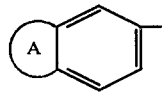

is selected from the group consisting of naphthyl, benzo [b] furanyl, benzo [b] thienyl, benzodioxolyl, benzodioxanyl, benzodioxacycloheptanyl, coumaranyl, chromanyl, $\Delta^3$-chromenyl, thiochromanyl and $\Delta^3$-thiochromenyl.

2. A compound of claim 1, wherein

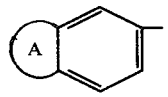

is selected from the group consisting of benzo [b] furanyl, benzodioxolyl, benzodioxanyl and coumaranyl.

3. A compound of claim 1 which is 1-piperonyl-4-(1,3,4-thiadiazol-2-yl)-piperazine.

4. A compound of claim 1, which is 1-(3,4-ethylenedioxybenzyl)-4-(1,3,4-thiadiazol-2-yl)-piperazine.

5. A compound of claim 1, which is 1-(5-benzo [b] furanylmethyl)-4-(1,3,4-thiadiazol-2yl)-piperazine.

6. A pharmaceutical composition for treating peripheral vascular disorders or Parkinson's disease containing as active ingredient an effective amount of a compound of claim 1, together with a suitable pharmaceutically acceptable carrier.

7. A method for treating a living animal body afflicted with peripheral vascular disorders or Parkinson's disease, comprising the step of administering an effective amount of a compound of claim 1 for the alleviation of the said conditions.

* * * * *

UNITED STATES PATENT OFFICE
CERTIFICATE OF CORRECTION

Patent No. 4,177,272          Dated December 4, 1979

Inventor(s) Gilbert Regnier et al

It is certified that error appears in the above-identified patent and that said Letters Patent are hereby corrected as shown below:

Column 1, line 37, delete "amino" and insert in place thereof --imino--.

Signed and Sealed this

Twenty-fifth Day of March 1980

[SEAL]

*Attest:*

SIDNEY A. DIAMOND

*Attesting Officer*          *Commissioner of Patents and Trademarks*